United States Patent [19]
Hudock

[11] Patent Number: 5,178,627
[45] Date of Patent: Jan. 12, 1993

[54] MEDICAL DEVICE FOR USE IN THE TREATMENT OF HEMORRHOIDS

[76] Inventor: Harriet Hudock, 259 White Oak Ridge Rd., Short Hills, N.J. 07078

[21] Appl. No.: 818,770

[22] Filed: Jan. 13, 1992

Related U.S. Application Data

[63] Continuation-in-part of Ser. No. 503,662, Apr. 3, 1990, abandoned.

[51] Int. Cl.$^5$ .............................................. A61M 29/00
[52] U.S. Cl. ................................... 606/197; 604/48; 604/104
[58] Field of Search ............ 606/191, 197, 198; 604/48, 104, 105, 286, 285; 128/401

[56] References Cited

U.S. PATENT DOCUMENTS

| | | | |
|---|---|---|---|
| 702,789 | 6/1902 | Gibson | 606/197 |
| 1,244,751 | 10/1917 | McCleary | 606/198 |
| 1,271,456 | 7/1918 | Flack | 606/197 |
| 1,610,947 | 12/1926 | Hosmer | 606/197 |
| 1,877,766 | 9/1932 | Kennedy | 606/197 |
| 1,879,307 | 9/1932 | Kennedy | 606/197 |
| 1,928,893 | 10/1933 | Hoard | 606/197 |
| 2,290,571 | 7/1942 | Peyton | 606/197 |
| 2,443,207 | 6/1948 | Tedford | 606/198 |
| 2,653,599 | 9/1953 | Bell | 606/191 |
| 2,721,549 | 10/1955 | Ferraro | 606/191 |
| 3,675,642 | 7/1972 | Lord | 606/197 |
| 3,826,242 | 7/1974 | Eggers | 606/197 |
| 4,257,406 | 3/1981 | Shenk | 606/197 |
| 4,583,542 | 4/1986 | Boyd | 606/197 |

Primary Examiner—C. Fred Rosebaum
Assistant Examiner—William W. Lewis
Attorney, Agent, or Firm—Lorraine M. Donaldson

[57] ABSTRACT

A device for treating hemorrhoids is formed from a hollow member having integral insertion and collar portions. Controlling means located within the member and running from the collar to at least partially the length of the insertion portion serve to control the maximum transverse section of the device. Reduction of the cross section eases insertion and extraction of the device. Release of the controlling means allows the device to resiliently return to its normal condition.

13 Claims, 1 Drawing Sheet

MEDICAL DEVICE FOR USE IN THE TREATMENT OF HEMORRHOIDS

CROSS REFERENCE TO RELATED PATENT APPLICATION

The present application is a continuation-in-part of my earlier patent application Ser. No. 07/503,662 filed Apr. 3, 1990, now abandoned.

BACKGROUND OF THE INVENTION

1. The Field of the Invention

The present invention relates to a medical device for use in the treatment of hemorrhoid problems.

2. The Prior Art

The veins of the internal rectal plexus often become excessively dilated and inflamed in a condition commonly known as hemorrhoids or piles. This inflammation and swelling of the veins located in the rectum and anus region is due to several factors. One is the vessels are contained in very loose connective tissue. Therefore, the rectal veins receive less support from surrounding tissues and are less able to resist increased blood pressure. Constipation, often the result of poor eating habits, further exacerbates the condition.

While the condition is generally not serious, in a life threatening sense, it is very common and can cause moderate to severe discomfort in patients during episodes in which the veins are particularly swollen. In fact, the defeat of Napoleon by Wellington at Waterloo in 1815 has been attributed, at least in part, to Napoleon's alleged inattention to the battle caused by his suffering from hemorrhoid problems.

Standard treatment consists of the application of creams or ointments, sitz baths, and, in more severe cases, surgical intervention. Further, a number of medical devices have been proposed to augment or supplant the above treatment methods by providing needed support to hold the protruding veins in place while the swelling and inflammation subside thus protecting the area from further injury.

U.S. Pat. No. 702,789 issued to Gibson on Jun. 17, 1902, discloses a dilator formed from a slender tube having longitudinal slits in communication with an internal pear-shaped piston which will cause the diameter of the tube to expand in the region of the piston when it is moved through the tube. The maximum variation of the external geometry of the device is limited by the practical limits of varying the wall thickness of the segmented tube. Further, Gibson does not address the benefits of using such a device for the treatment of hemorrhoids.

U.S. Pat. No. 1,271,456 issued to Flack discloses a rectal dilator which, while it is expansible, would clearly require the assistance of someone to aid the patient in effecting the expansion of the device once it is in place. This is because the device is screw operated and would necessarily have to be held against rotation while the knob 10 is twisted. Clearly this device, as is the case with the above mentioned Gibson device, could not be worn by the patient during the daily routine.

U.S. Pat. No. 1,610,946 issued to Hosmer on Dec. 14, 1926, discloses a medical device (sometimes referred to as a "bougie") for the treatment of the disorder. The device has a rigid conical shape having spiral ridges on its outer surface. This instrument provides no means for adjusting pressure by conveniently changing the geometry of the device during the insertion and/or removal operation.

U.S. Pat. No. 2,653,599 issued to Bell on Sep. 29, 1953, discloses an instrument having a shank of uniform diameter with a partial sphere-structure which is adapted to be inserted into the rectum. The other end is fitted with a stop having the face thereof nearest to the partial sphere of convex shape. Again, no provision is made or suggested for changing the geometry of the device during use to permit easy insertion or removal or to control the pressure applied to the rectal wall.

U.S. Pat. No. 3,675,642 issued to Lord on Jul. 11, 1972, discloses a rectal cone for use in post operative care of hemorrhoidectomy and similar procedures. The cone's maximum diameter is required to be approximately 1.5 inches. Further, the medical instrument has no provision for changing the geometry of the instrument in use.

Various dilating instruments have been designed to stretch or expand tissues or cavities with each instrument specially adapted to its particular function. Representative of the genre is U.S. Pat. No. 4,257,406, which discloses an iris retractor and pupil dilator. This instrument uses a pair of cross-action spring arms designed to expand the pupil to permit removal of the lens without injury to the iris. This instrument is designed for making small tweezer-like movements for use in eye surgery. U.S. Pat. No. 1,928,893 discloses a vaginal and rectal exerciser formed by a pair of semi cylindrical members spring loaded with respect to each other.

U.S. Pat. Nos. 1,244,751; 1,877,766; 1,879,307; 2,443,207; 2,721,549; 3,826,242; and 4,583,542 disclose other variations of instruments designed to treat hemorrhoids and are on general interest.

The prior art does not provide a hemorrhoid instrument that is easily adjusted for insertion and removal yet is capable of providing sufficient pressure to hold protruding hemorrhoids in place while healing occurs.

SUMMARY OF THE INVENTION

The present invention is medical device for the treatment of hemorrhoids and is formed with a substantially hollow insertable member having a flexible, resilient wall with an insertable tip at one end and a neck opposite to the tip toward the opposite end with the insertable tip having a transverse section along its length which is substantially circular and a longitudinal section which is substantially parabolic in the region of the tip flaring to provide a maximum transverse diameter adjacent to the midpoint between the tip and the neck and progressively diminishing from the point of maximum transverse diameter to provide a minimum transverse diameter at the neck. A substantially hollow collar, having a flexible, resilient wall formed into a substantially truncated conical shape, has its minimum transverse diameter integrally attached to the neck of the insertable section with its maximum transverse diameter farthest from the tip of said insertable tip. Controlling arm means extend at least partially the length of the tip and are actuated scissor fashion for selecting the transverse cross sectional diameter of the insertable section by manipulating the collar single-handedly using the thumb and forefinger. The arm means deform the member form its relaxed state to which it returns when the arms are released.

It is an object of the present invention to provide a hemorrhoid treating device which can be adjusted onehandedly to provide a small insertion and removal geometry but which is self expanding upon placement to an overall size which permits maximum medical benefit.

It is another object of the invention to provide a hemorrhoid treating device that has all parts in contact with the patient fabricated from hypo-allergenic material.

It is still another object of the invention to provide a hemorrhoid treatment device that can be color coded to identify the correct end of the device to be inserted into the patient as well as other features such a size, lubrication, and medication carried by the device.

It is a further object of the invention to provide a hemorrhoid treatment device that is held in place by flexible, non-irritating collar.

It is a final object of the invention to provide a pre-lubricated and pre-medicated hemorrhoid treatment device that is disposable.

BRIEF DESCRIPTION OF THE DRAWINGS

The present invention will now be described, by way of example, with reference to the accompanying drawings, in which.

DETAILED DESCRIPTION OF THE PREFERRED EMBODIMENT

Figure 1:
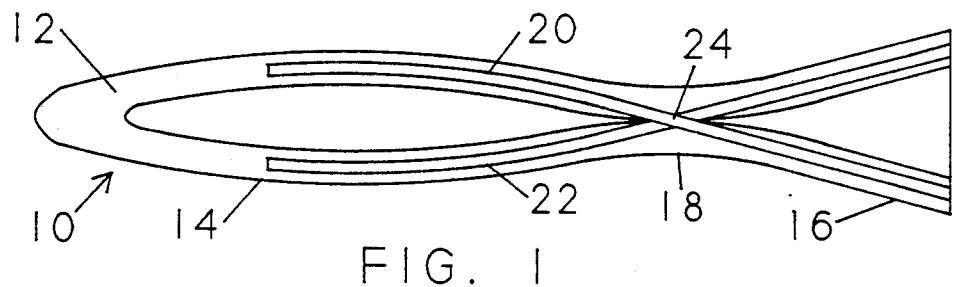
FIG. 1 is a longitudinal section through the hemorrhoid treatment device according to the present invention in its expanded or normal mode.
Figure 2:
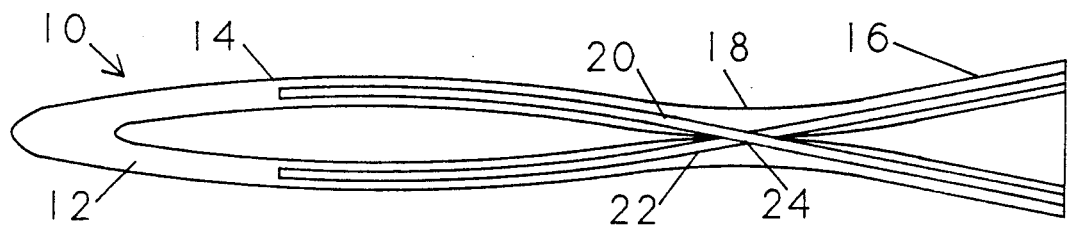
FIG. 2 is a longitudinal section through the hemorrhoid treatment device according to the present invention in its contracted or insertion/removal mode.
Figure 3:
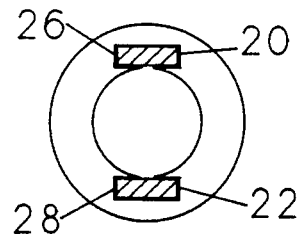
FIG. 3 is a transverse section taken along line 3—of FIG. 1 showing the controlling means retaining grooves.

The subject invention is shown in longitudinal section in FIGS. 1 and 2. The subject hemorrhoid treatment device 10 is preferably fabricated from hypo-allergenic material, such as medical-grade silicone rubber or other material having similar flexible properties. The subject device 10 has a hollow body 12 with a generally parabolic insertion portion 14 integrally joined to a generally truncated conical collar portion 16 at neck portion 18. Actuation means are formed by first and second arms 20,22 which are connected at point 24 in scissor like fashion. The arms 20,22 are substantially identical and are preferably formed from single pieces of metal, such as stainless steel, that will enable the body to stay in its normally expanded shape to present its maximum transverse cross section. The body of the subject device is preferably formed with internal slots or grooves 26,28, each receiving a respective one of these arms 20,22. These slots or grooves 26,28 are best seen in FIG. 3 and are preferably transversely profiled to receive and retain a respective arm member 20,22 therein.

Typically the subject device would be molded by known injection molding processes. The device would preferably have a skin thickness of approximately 3/32" and have an overall length of approximately 1⅜", greatest diameter of ½", and neck or smallest diameter of approximately ¼". The arms typically would be ⅛" wide, 1/16" thick and ¾" long.

In order to insert the subject invention, the patient would grasp the collar portion 16 between thumb and forefinger and compress it to squeeze the ends 30,32 of the arms 20,22 causing them to rotate about their common point of articulation 24. This causes the other ends 34,36 of the arms 20,22 to follow a like inward rotational movement pulling in the wall of the device thereby reducing the overall transverse cross sectional shape of the device together with causing a slight a slight elongation, as seen in FIG. 2. This reduced transverse cross section allows for insertion of the device into the anus with less frictional engagement with the walls of the rectum and thus with less discomfort to the patient. When properly positioned, which is determined by engagement of the collar portion 16 against the patient, the ends 30,32 of the arms 20,22 are released. This causes the device 10 to resiliently expand to its normal position, as shown in FIG. 1, pressing against the distended veins.

The subject device is preferably used with a known lubricant, such as vaseline, KY jelly, or similar products. This could be either in the form of a prelubricated device or the patient/user could apply the lubricant immediately prior to use.

While the present invention has been shown in the preferred form with a smooth outer surface, either the entire surface or only the tip portion could be formed with one or more uniformly disposed pores for containing medicaments for release, such as by time release, during use of the device. The medicants would speed the healing process.

The size and number of pores would be determined by the particular medication to be dispensed. Typically the pore size would be on the order of 1/32 of an inch in diameter and located at spaced ¼" intervals.

Figure 4:
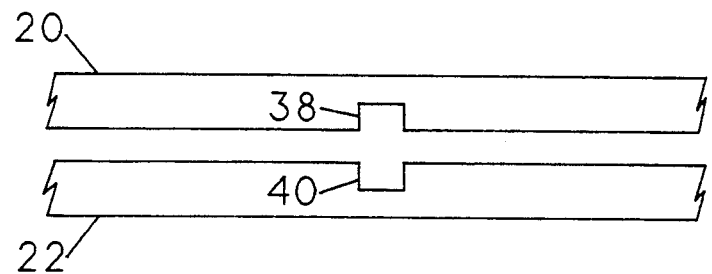
FIG. 4 is a detailed view of means for locking the arms together.

It is also within the preview of the present invention to provide color coding to clearly identify which end of the subject device is to be inserted. This color coding could be expanded to include identification of the above mentioned embodiments containing medications to both identify that type of device (prelubricated and/or containing medication) as well as the type of medication. It would be further within the scope of the invention to used the color coding to identify the size of the device and the strength of the arms so that the correct size device and the correct amount of pressure could be selected.

the arms 20,22 have been shown in FIG. 4 with interlocking notches 38,40, which is an inexpensive and convenient method of joining the arms for articulation. However, the arms could be replaced with wires (not shown) of sufficient gauge and elastic modulus to permit tensioning of the invention in the above described manner. An appropriate means (also not shown) would be necessary for joining the wires for articulation.

The present invention may be subject to many changes and modifications without departing from the spirit or essential characteristics thereof as defined by the appended claims.

I claim:

1. A medical device for the treatment of hemorrhoids comprising:

a substantially hollow insertable member having a flexible, resilient wall with an insertable tip at one end and a neck opposite to said tip toward the opposite end with said insertable tip having a transverse section along its length which is substantially circular and a longitudinal section which is substantially parabolic in the region of said tip flaring to provide a maximum transverse diameter adjacent to the midpoint between the tip and the neck and progressively diminishing from the point of maximum transverse diameter to provide a minimum transverse diameter at the neck;

a substantially hollow collar having a flexible, resilient wall formed into a substantially truncated conical shape with its minimum transverse diameter attached to the neck of said insertable section and its maximum transverse diameter farthest from the tip of said insertable tip;

controlling means extending from said collar to at least partially down the length of said insertable section for selecting the transverse diameter of said insertable section by manipulating said collar single-handedly using the thumb and forefinger causing the walls of said insertable section to be drawn inwardly.

2. The medical device of claim 1 wherein said controlling means further comprises:

a plurality of arm members;

a like plurality of longitudinal opposing slots in the wall of said insertable portion with each slot corresponding to one of the arm members;

a like plurality of longitudinal opposing slots in the wall of said collar with each slot corresponding to one of the arm members;

each arm member is fitted within its slot under compression with the arm members crossing in the region adjacent to the neck of said insertable section; and wherein when said collar is compressed towards the longitudinal axis of the instrument on opposite points in the region of maximum transverse diameter, the walls of said insertable section move towards one another to reduce the transverse diameter and when said collar is released the walls of said insertable section resiliently regain their maximum transverse dimension.

3. The medical device of claim 2 wherein said insertable portion and collar are fabricated from hypo-allergenic material.

4. The medical device of claim 3 wherein said insertable portion and collar are integral.

5. The medical device of claim 4 wherein the tip of said insertable portion is open.

6. The medical device of claim 5 wherein the tip of said insertable portion contains medicaments suitable for treatment of hemorrhoids.

7. The medical device of claim 6 wherein said arm members are notched so that one arm member may be movably joined to its opposing arm member.

8. The medical device of claim 7 wherein said arm members are fabricated out of steel.

9. The medical device of claim 8 wherein the overall length of said instrument is at least one and three eighths inches long.

10. The medical device of claim 9 wherein the maximum transverse diameter of said insertable section is one half inch.

11. The medical device of claim 10 wherein the neck of said insertable section is at least one quarter of an inch in diameter.

12. The medical device of claim 2 wherein the arm members are fabricated from wire of sufficient gauge and elastic modulus to cause the insertable portion to reach its efficacious transverse diameter during use.

13. The medical device of claim 2 wherein the walls of said insertable portion contain a plurality of pores distributed substantially evenly from one another with each pore size and distance from an adjacent pore corresponding to a medicament placed within said insertable portion.

* * * * *